US008083879B2

(12) United States Patent
Swinehart et al.

(10) Patent No.: US 8,083,879 B2
(45) Date of Patent: Dec. 27, 2011

(54) NON-METALLIC, MULTI-STRAND CONTROL CABLE FOR STEERABLE INSTRUMENTS

(75) Inventors: Charles Swinehart, San Jose, CA (US);
Lawrence Kerver, Los Gatos, CA (US);
Chris Julian, Los Gatos, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 1364 days.

(21) Appl. No.: 11/604,019

(22) Filed: Nov. 22, 2006

(65) Prior Publication Data

US 2007/0161291 A1 Jul. 12, 2007

Related U.S. Application Data

(60) Provisional application No. 60/739,250, filed on Nov. 23, 2005.

(51) Int. Cl.
*B29C 65/02* (2006.01)
*B29C 65/48* (2006.01)
*A61M 25/09* (2006.01)
*A61B 1/01* (2006.01)

(52) U.S. Cl. ....... 156/158; 156/293; 29/433; 604/95.04; 600/146

(58) Field of Classification Search .................. 156/158, 156/293, 294; 29/433, 241; 600/146, 149; 604/95.04, 528
See application file for complete search history.

(56) References Cited

U.S. PATENT DOCUMENTS

| 616,672 | A | 12/1898 | Kelling |
| 2,510,198 | A | 6/1950 | Tesmer |
| 2,533,494 | A | 12/1950 | Mitchell, Jr. |
| 2,767,705 | A | 10/1956 | Moore |
| 3,060,972 | A | 10/1962 | Sheldon |
| 3,071,161 | A | 1/1963 | Ulrich |
| 3,096,962 | A | 7/1963 | Meijs |
| 3,162,214 | A | 12/1964 | Bazinet, Jr. |
| 3,168,274 | A | 2/1965 | Street |
| 3,190,286 | A | 6/1965 | Stokes |
| 3,266,059 | A | 8/1966 | Stelle |
| 3,430,662 | A | 3/1969 | Guarnaschelli |
| 3,497,083 | A | 2/1970 | Anderson |
| 3,546,961 | A | 12/1970 | Marton |
| 3,610,231 | A | 10/1971 | Takahashi |
| 3,625,084 | A | 12/1971 | Low |

(Continued)

FOREIGN PATENT DOCUMENTS

DE 2823025 12/1979

(Continued)

OTHER PUBLICATIONS

Durant, et al.; U.S. Appl. No. 12/036,976 entitled "Systems and methods for articulating an elongate body," filed Feb. 25, 2008.

(Continued)

*Primary Examiner* — Michael Tolin

(57) ABSTRACT

Embodiments of the invention provide methods for inserting a non-metallic multi-strand braid through a coil tube. Techniques for bonding one end of a lead line to one end of a multi-strand non-metallic braid are provided. There are also embodiments of steerable instruments described having a plurality of hinged segments; a multi-strand non-metallic braid connected distally to one segment of the plurality of segments and proximally to an actuator; and a steering controller adapted to control the actuator to move the hinged segment using the multi-strand non-metallic braid.

15 Claims, 9 Drawing Sheets

U.S. PATENT DOCUMENTS

| | | |
|---|---|---|
| 3,643,653 A | 2/1972 | Takahashi et al. |
| 3,739,770 A | 6/1973 | Mori |
| 3,773,034 A | 11/1973 | Burns et al. |
| 3,780,740 A | 12/1973 | Rhea |
| 3,858,578 A | 1/1975 | Milo |
| 3,871,358 A | 3/1975 | Fukuda et al. |
| 3,897,775 A | 8/1975 | Furihata |
| 3,913,565 A | 10/1975 | Kawahara |
| 3,946,727 A | 3/1976 | Okada |
| 3,990,434 A | 11/1976 | Free |
| 4,054,128 A | 10/1977 | Seufert |
| 4,176,662 A | 12/1979 | Frazer |
| 4,233,981 A | 11/1980 | Schomacher |
| 4,236,509 A | 12/1980 | Takahashi |
| 4,240,435 A | 12/1980 | Yazawa et al. |
| 4,273,111 A | 6/1981 | Tsukaya |
| 4,327,711 A | 5/1982 | Takagi |
| 4,366,810 A | 1/1983 | Slanetz, Jr. |
| 4,393,728 A | 7/1983 | Larson |
| 4,432,349 A | 2/1984 | Oshiro |
| 4,483,326 A | 11/1984 | Yamaka et al. |
| 4,489,826 A | 12/1984 | Dubson |
| 4,494,417 A | 1/1985 | Larson |
| 4,499,895 A | 2/1985 | Takayama |
| 4,503,842 A | 3/1985 | Takayama |
| 4,543,090 A | 9/1985 | McCoy |
| 4,551,061 A | 11/1985 | Olenick |
| 4,559,928 A | 12/1985 | Takayama |
| 4,566,843 A | 1/1986 | Iwatsuka |
| 4,577,621 A | 3/1986 | Patel |
| 4,592,341 A | 6/1986 | Omagari et al. |
| 4,601,283 A | 7/1986 | Chikama |
| 4,601,713 A | 7/1986 | Fuqua |
| 4,621,618 A | 11/1986 | Omagari |
| 4,624,243 A | 11/1986 | Lowery et al. |
| 4,630,649 A | 12/1986 | Oku |
| 4,643,184 A | 2/1987 | Mobin-Uddin |
| 4,646,722 A | 3/1987 | Silverstein et al. |
| 4,648,733 A | 3/1987 | Merkt |
| 4,651,718 A | 3/1987 | Collins et al. |
| 4,655,257 A | 4/1987 | Iwashita |
| 4,683,773 A | 8/1987 | Diamond |
| 4,686,963 A | 8/1987 | Cohen et al. |
| 4,712,969 A | 12/1987 | Kimura |
| 4,726,355 A | 2/1988 | Okada |
| 4,753,222 A | 6/1988 | Morishita |
| 4,753,223 A | 6/1988 | Bremer |
| 4,754,909 A | 7/1988 | Barker et al. |
| 4,784,117 A | 11/1988 | Miyazaki |
| 4,787,369 A | 11/1988 | Allred, III |
| 4,788,967 A | 12/1988 | Ueda |
| 4,793,326 A | 12/1988 | Shishido |
| 4,796,607 A | 1/1989 | Allred, III |
| 4,799,474 A | 1/1989 | Ueda |
| 4,800,890 A | 1/1989 | Cramer |
| 4,807,593 A | 2/1989 | Ito |
| 4,815,450 A | 3/1989 | Patel |
| 4,832,473 A | 5/1989 | Ueda |
| 4,834,068 A | 5/1989 | Gottesman |
| 4,873,965 A | 10/1989 | Danieli |
| 4,873,990 A | 10/1989 | Holmes et al. |
| 4,879,991 A | 11/1989 | Ogiu |
| 4,884,557 A | 12/1989 | Takehana et al. |
| 4,890,602 A | 1/1990 | Hake |
| 4,895,431 A | 1/1990 | Tsujiuchi et al. |
| 4,899,731 A | 2/1990 | Takayama et al. |
| 4,904,048 A | 2/1990 | Sogawa et al. |
| 4,917,114 A | 4/1990 | Green et al. |
| 4,919,112 A | 4/1990 | Siegmund |
| 4,930,494 A | 6/1990 | Takehana et al. |
| 4,949,927 A | 8/1990 | Madocks et al. |
| 4,957,486 A | 9/1990 | Davis |
| 4,969,709 A | 11/1990 | Sogawa et al. |
| 4,971,035 A | 11/1990 | Ito |
| 4,977,886 A | 12/1990 | Takehana et al. |
| 4,977,887 A | 12/1990 | Gouda |
| 4,987,314 A | 1/1991 | Gotanda et al. |
| 5,005,558 A | 4/1991 | Aomori |
| 5,005,559 A | 4/1991 | Blanco et al. |
| 5,014,709 A | 5/1991 | Bjelkhagen et al. |
| 5,018,509 A | 5/1991 | Suzuki et al. |
| 5,025,778 A | 6/1991 | Silverstein et al. |
| 5,060,632 A | 10/1991 | Hibino et al. |
| 5,092,901 A | 3/1992 | Hunter et al. |
| 5,125,395 A | 6/1992 | Adair |
| 5,127,393 A | 7/1992 | McFarlin et al. |
| 5,159,446 A | 10/1992 | Hibino et al. |
| 5,166,787 A | 11/1992 | Irion |
| 5,174,276 A | 12/1992 | Crockard |
| 5,174,277 A | 12/1992 | Matsumaru |
| 5,188,111 A | 2/1993 | Yates et al. |
| 5,207,695 A | 5/1993 | Trout, III |
| 5,217,001 A | 6/1993 | Nakao et al. |
| 5,220,911 A | 6/1993 | Tamura |
| 5,228,429 A | 7/1993 | Hatano |
| 5,234,448 A | 8/1993 | Wholey et al. |
| 5,243,967 A | 9/1993 | Hibino |
| 5,250,058 A | 10/1993 | Miller et al. |
| 5,251,611 A | 10/1993 | Zehel et al. |
| 5,253,647 A | 10/1993 | Takahashi |
| 5,254,809 A | 10/1993 | Martin |
| 5,257,617 A | 11/1993 | Takahashi |
| 5,259,364 A | 11/1993 | Bob et al. |
| 5,271,381 A | 12/1993 | Ailinger et al. |
| 5,271,382 A | 12/1993 | Chikama |
| 5,279,610 A | 1/1994 | Park et al. |
| 5,297,443 A | 3/1994 | Wentz |
| 5,325,845 A | 7/1994 | Adair |
| 5,334,145 A * | 8/1994 | Lundquist et al. ......... 604/95.04 |
| 5,337,732 A | 8/1994 | Grundfest et al. |
| 5,337,733 A | 8/1994 | Bauerfeind |
| 5,343,874 A | 9/1994 | Picha |
| 5,347,987 A | 9/1994 | Feldstin et al. |
| 5,348,259 A | 9/1994 | Blanco et al. |
| 5,370,108 A | 12/1994 | Miura et al. |
| 5,383,467 A | 1/1995 | Auer et al. |
| 5,383,852 A | 1/1995 | Stevens-Wright |
| 5,389,222 A | 2/1995 | Shahinpoor |
| 5,394,864 A | 3/1995 | Kobayashi et al. |
| 5,400,769 A | 3/1995 | Tanii et al. |
| 5,402,768 A | 4/1995 | Adair |
| 5,411,508 A | 5/1995 | Bessler et al. |
| 5,413,108 A | 5/1995 | Alfano |
| 5,421,337 A | 6/1995 | Richards-Kortum et al. |
| 5,425,738 A | 6/1995 | Gustafson et al. |
| 5,429,118 A | 7/1995 | Cole et al. |
| 5,439,000 A | 8/1995 | Gunderson et al. |
| 5,451,221 A | 9/1995 | Cho et al. |
| 5,456,714 A | 10/1995 | Owen |
| 5,460,166 A | 10/1995 | Yabe et al. |
| 5,460,168 A | 10/1995 | Masubuchi et al. |
| 5,462,527 A * | 10/1995 | Stevens-Wright et al. ... 604/528 |
| 5,469,840 A | 11/1995 | Tanii et al. |
| 5,482,029 A | 1/1996 | Sekiguchi et al. |
| 5,487,757 A | 1/1996 | Truckai et al. |
| 5,489,256 A | 2/1996 | Adair |
| 5,507,287 A | 4/1996 | Palcic et al. |
| 5,507,717 A | 4/1996 | Kura et al. |
| 5,531,664 A | 7/1996 | Adachi et al. |
| 5,551,945 A | 9/1996 | Yabe et al. |
| 5,558,619 A | 9/1996 | Kami et al. |
| 5,558,665 A | 9/1996 | Kieturakis |
| 5,577,992 A | 11/1996 | Chiba et al. |
| 5,586,968 A | 12/1996 | Grundl et al. |
| 5,590,660 A | 1/1997 | MacAulay et al. |
| 5,601,087 A | 2/1997 | Gunderson et al. |
| 5,602,449 A | 2/1997 | Krause |
| 5,620,408 A | 4/1997 | Vennes et al. |
| 5,624,380 A | 4/1997 | Takayama et al. |
| 5,624,381 A | 4/1997 | Kieturakis |
| 5,626,553 A | 5/1997 | Frassica et al. |
| 5,645,520 A | 7/1997 | Nakamura et al. |
| 5,647,368 A | 7/1997 | Zeng et al. |
| 5,651,769 A | 7/1997 | Waxman et al. |
| 5,653,690 A | 8/1997 | Booth et al. |
| 5,658,238 A | 8/1997 | Suzuki et al. |
| 5,662,585 A | 9/1997 | Willis et al. |

| | | | | | |
|---|---|---|---|---|---|
| 5,662,587 A | 9/1997 | Grundfest et al. | 6,249,076 B1 | 6/2001 | Madden et al. |
| 5,665,050 A | 9/1997 | Benecke | 6,270,453 B1 | 8/2001 | Sakai |
| 5,667,476 A | 9/1997 | Frassica et al. | 6,306,081 B1 | 10/2001 | Ishikawa et al. |
| 5,679,216 A | 10/1997 | Takayama et al. | 6,309,346 B1 | 10/2001 | Farhadi |
| 5,728,044 A | 3/1998 | Shan | 6,315,714 B1 | 11/2001 | Akiba |
| 5,733,245 A | 3/1998 | Kawano | 6,319,197 B1 | 11/2001 | Tsuji et al. |
| 5,749,828 A | 5/1998 | Solomon et al. | 6,327,492 B1 | 12/2001 | Lemelson |
| 5,752,912 A | 5/1998 | Takahashi et al. | 6,332,089 B1 | 12/2001 | Acker |
| 5,759,151 A | 6/1998 | Sturges | 6,348,058 B1 | 2/2002 | Melkent |
| 5,762,613 A | 6/1998 | Sutton et al. | 6,366,799 B1 | 4/2002 | Acker |
| 5,765,561 A | 6/1998 | Chen et al. | 6,402,687 B1 | 6/2002 | Ouchi |
| 5,769,792 A | 6/1998 | Palcic et al. | 6,408,889 B1 | 6/2002 | Komachi |
| 5,772,597 A | 6/1998 | Goldberg | 6,428,203 B1 | 8/2002 | Danley |
| 5,773,835 A | 6/1998 | Sinofsky | 6,443,888 B1 | 9/2002 | Ogura et al. |
| 5,779,624 A | 7/1998 | Chang | 6,453,190 B1 | 9/2002 | Acker |
| 5,807,241 A | 9/1998 | Heimberger | 6,459,481 B1 | 10/2002 | Schaack |
| 5,810,715 A | 9/1998 | Moriyama | 6,468,203 B2 | 10/2002 | Belson |
| 5,810,716 A | 9/1998 | Mukherjee | 6,482,149 B1 | 11/2002 | Torii |
| 5,810,717 A | 9/1998 | Maeda | 6,485,413 B1 | 11/2002 | Boppart |
| 5,810,776 A | 9/1998 | Bacich et al. | 6,490,467 B1 | 12/2002 | Bucholz |
| 5,813,976 A | 9/1998 | Filipi et al. | 6,511,417 B1 | 1/2003 | Taniguchi et al. |
| 5,827,190 A | 10/1998 | Palcic et al. | 6,511,418 B2 | 1/2003 | Shahidi |
| 5,842,973 A | 12/1998 | Bullard | 6,517,477 B1 | 2/2003 | Wendlandt |
| 5,860,581 A | 1/1999 | Robertson et al. | 6,527,706 B2 | 3/2003 | Ide |
| 5,860,914 A | 1/1999 | Chiba et al. | 6,537,211 B1 | 3/2003 | Wang et al. |
| 5,876,329 A | 3/1999 | Harhen | 6,544,215 B1 | 4/2003 | Bencini et al. |
| 5,876,373 A | 3/1999 | Giba et al. | 6,554,793 B1 | 4/2003 | Pauker et al. |
| 5,885,208 A | 3/1999 | Moriyama | 6,569,173 B1 | 5/2003 | Blatter et al. |
| 5,893,369 A | 4/1999 | LeMole | 6,603,993 B1 | 8/2003 | Coutts et al. |
| 5,897,417 A | 4/1999 | Grey | 6,616,600 B2 | 9/2003 | Pauker |
| 5,897,488 A | 4/1999 | Ueda | 6,638,213 B2 | 10/2003 | Ogura et al. |
| 5,902,254 A | 5/1999 | Magram | 6,641,528 B2 | 11/2003 | Torii |
| 5,906,591 A | 5/1999 | Dario et al. | 6,656,110 B1 | 12/2003 | Irion et al. |
| 5,908,381 A | 6/1999 | Aznoian et al. | 6,699,183 B1 | 3/2004 | Wimmer |
| 5,916,147 A | 6/1999 | Boury | 6,761,685 B2 | 7/2004 | Adams et al. |
| 5,921,915 A | 7/1999 | Aznoian et al. | 6,783,491 B2 | 8/2004 | Saadat et al. |
| 5,928,136 A | 7/1999 | Barry | 6,790,173 B2 | 9/2004 | Saadat et al. |
| 5,941,815 A | 8/1999 | Chang | 6,800,056 B2 | 10/2004 | Tartaglia et al. |
| 5,941,908 A | 8/1999 | Goldsteen et al. | 6,808,499 B1 | 10/2004 | Churchill et al. |
| 5,957,833 A | 9/1999 | Shan | 6,808,520 B1 | 10/2004 | Fourkas et al. |
| 5,968,052 A | 10/1999 | Sullivan et al. | 6,817,973 B2 | 11/2004 | Merril et al. |
| 5,971,767 A | 10/1999 | Kaufman et al. | 6,837,846 B2 | 1/2005 | Jaffe |
| 5,976,074 A | 11/1999 | Moriyama | 6,837,847 B2 | 1/2005 | Ewers et al. |
| 5,989,182 A | 11/1999 | Hori et al. | 6,837,849 B2 | 1/2005 | Ogura et al. |
| 5,989,230 A | 11/1999 | Frassica | 6,843,793 B2 | 1/2005 | Brock et al. |
| 5,993,381 A | 11/1999 | Ito | 6,850,794 B2 | 2/2005 | Shahidi |
| 5,993,447 A | 11/1999 | Blewett et al. | 6,858,005 B2 | 2/2005 | Ohline |
| 5,996,346 A | 12/1999 | Maynard | 6,869,396 B2 | 3/2005 | Belson |
| 6,016,440 A | 1/2000 | Simon et al. | 6,875,170 B2 | 4/2005 | Francois et al. |
| 6,033,359 A | 3/2000 | Doi | 6,890,297 B2 | 5/2005 | Belson |
| 6,036,636 A | 3/2000 | Motoki et al. | 6,902,528 B1 | 6/2005 | Garibaldi et al. |
| 6,042,155 A | 3/2000 | Lockwood | 6,942,613 B2 | 9/2005 | Ewers et al. |
| 6,048,307 A | 4/2000 | Grundl et al. | 6,960,161 B2 | 11/2005 | Amiling et al. |
| 6,055,350 A * | 4/2000 | Brown et al. ............... 385/100 | 6,960,162 B2 | 11/2005 | Saadat et al. |
| 6,063,022 A | 5/2000 | Ben-Haim | 6,960,163 B2 | 11/2005 | Ewers et al. |
| 6,066,102 A | 5/2000 | Townsend et al. | 6,974,411 B2 | 12/2005 | Belson |
| 6,066,132 A | 5/2000 | Chen et al. | 6,984,203 B2 | 1/2006 | Tartaglia et al. |
| 6,068,638 A | 5/2000 | Makower | 7,018,331 B2 | 3/2006 | Chang et al. |
| 6,096,289 A | 8/2000 | Goldenberg | 7,087,013 B2 | 8/2006 | Belson et al. |
| 6,099,464 A | 8/2000 | Shimizu et al. | 2002/0016607 A1 | 2/2002 | Bonadio et al. |
| 6,099,465 A | 8/2000 | Inoue | 2002/0062062 A1 | 5/2002 | Belson et al. |
| 6,099,485 A | 8/2000 | Patterson | 2002/0120254 A1 | 8/2002 | Julian |
| 6,106,510 A | 8/2000 | Lunn et al. | 2002/0147385 A1 | 10/2002 | Butler et al. |
| 6,119,913 A | 9/2000 | Adams et al. | 2002/0151767 A1 | 10/2002 | Sonnenschein |
| 6,129,667 A | 10/2000 | Dumoulin et al. | 2002/0169361 A1 | 11/2002 | Taniguchi |
| 6,129,683 A | 10/2000 | Sutton et al. | 2002/0193662 A1 | 12/2002 | Belson |
| 6,141,577 A | 10/2000 | Roland | 2003/0083550 A1 | 5/2003 | Miyagi |
| 6,149,581 A | 11/2000 | Klingenstein | 2003/0130598 A1 | 7/2003 | Manning et al. |
| 6,162,171 A | 12/2000 | Ng et al. | 2003/0167007 A1 | 9/2003 | Belson |
| 6,174,280 B1 | 1/2001 | Oneda | 2003/0182091 A1 | 9/2003 | Kukuk |
| 6,174,291 B1 | 1/2001 | McMahon et al. | 2003/0195387 A1 | 10/2003 | Kortenbach et al. |
| 6,179,776 B1 | 1/2001 | Adams | 2003/0233056 A1 | 12/2003 | Saadat et al. |
| 6,185,448 B1 | 2/2001 | Borovsky | 2003/0236505 A1 | 12/2003 | Bonadio et al. |
| 6,201,989 B1 | 3/2001 | Whitehead | 2003/0236549 A1 | 12/2003 | Bonadio et al. |
| 6,203,493 B1 | 3/2001 | Ben-Haim | 2004/0019254 A1 | 1/2004 | Belson |
| 6,203,494 B1 | 3/2001 | Moriyama | 2004/0044270 A1 | 3/2004 | Barry |
| 6,210,337 B1 | 4/2001 | Dunham et al. | 2004/0049251 A1 | 3/2004 | Knowlton |
| 6,221,006 B1 | 4/2001 | Dubrul et al. | 2004/0097788 A1 | 5/2004 | Mourlas et al. |
| 6,241,657 B1 | 6/2001 | Chen et al. | 2004/0106852 A1 | 6/2004 | Windheuser et al. |

| | | | |
|---|---|---|---|
| 2004/0176683 A1 | 9/2004 | Whitin et al. | |
| 2004/0186350 A1 | 9/2004 | Brenneman et al. | |
| 2004/0193008 A1 | 9/2004 | Jaffe et al. | |
| 2004/0193009 A1 | 9/2004 | Jaffe et al. | |
| 2004/0210109 A1 | 10/2004 | Jaffe et al. | |
| 2004/0220450 A1 | 11/2004 | Jaffe et al. | |
| 2004/0230096 A1 | 11/2004 | Stefanchik et al. | |
| 2005/0020901 A1 | 1/2005 | Belson et al. | |
| 2005/0059925 A1 | 3/2005 | Maginot et al. | |
| 2005/0085693 A1 | 4/2005 | Belson et al. | |
| 2005/0124855 A1 | 6/2005 | Jaffe et al. | |
| 2005/0137454 A1 | 6/2005 | Saadat et al. | |
| 2005/0137455 A1 | 6/2005 | Ewers et al. | |
| 2005/0137456 A1 | 6/2005 | Saadat et al. | |
| 2005/0154258 A1 | 7/2005 | Tartaglia et al. | |
| 2005/0154261 A1 | 7/2005 | Ohline et al. | |
| 2005/0165276 A1 | 7/2005 | Belson | |
| 2005/0168571 A1 | 8/2005 | Lia et al. | |
| 2005/0203339 A1 | 9/2005 | Butler et al. | |
| 2005/0209506 A1 | 9/2005 | Butler et al. | |
| 2005/0209509 A1 | 9/2005 | Belson | |
| 2005/0222497 A1 | 10/2005 | Belson | |
| 2005/0222498 A1 | 10/2005 | Belson | |
| 2005/0250990 A1 | 11/2005 | Le et al. | |
| 2006/0009678 A1 | 1/2006 | Jaffe et al. | |
| 2006/0052664 A1 | 3/2006 | Julian et al. | |
| 2006/0074383 A1* | 4/2006 | Boulais | 604/95.04 |
| 2006/0235457 A1 | 10/2006 | Belson | |
| 2006/0235458 A1 | 10/2006 | Belson | |
| 2006/0258912 A1 | 11/2006 | Belson et al. | |
| 2007/0043259 A1 | 2/2007 | Jaffe et al. | |
| 2007/0093858 A1 | 4/2007 | Gambale et al. | |
| 2007/0135803 A1 | 6/2007 | Belson | |
| 2007/0161857 A1 | 7/2007 | Durant et al. | |
| 2007/0249901 A1 | 10/2007 | Ohline et al. | |
| 2007/0270650 A1 | 11/2007 | Eno et al. | |
| 2008/0154288 A1 | 6/2008 | Belson | |

FOREIGN PATENT DOCUMENTS

| | | |
|---|---|---|
| DE | 8807771 U1 | 8/1988 |
| DE | 3707787 | 9/1988 |
| DE | 4102211 A1 | 8/1991 |
| DE | 19626433 A1 | 1/1998 |
| DE | 19729499 A1 | 1/1999 |
| EP | 0165718 A2 | 12/1985 |
| EP | 0382974 A1 | 8/1990 |
| EP | 0497781 B1 | 1/1994 |
| EP | 0993804 A1 | 4/2000 |
| EP | 1101442 A2 | 5/2001 |
| EP | 1681013 A1 | 7/2006 |
| FR | 2732225 A1 | 10/1996 |
| GB | 1354209 A | 6/1974 |
| GB | 2347685 A | 9/2000 |
| IE | 2000/0225 | 3/2000 |
| IE | 2000/0559 | 7/2000 |
| IE | 2002/0170 | 3/2002 |
| JP | 63136014 | 6/1988 |
| JP | 63272322 | 11/1988 |
| JP | 1152413 | 6/1989 |
| JP | 1229220 | 9/1989 |
| JP | 01-262372 | 10/1989 |
| JP | 2246986 | 10/1990 |
| JP | 2296209 | 12/1990 |
| JP | 3136630 | 6/1991 |
| JP | 4054970 | 2/1992 |
| JP | 5011196 | 1/1993 |
| JP | 5111458 | 5/1993 |
| JP | 5305073 | 11/1993 |
| JP | 06-007287 | 1/1994 |
| JP | 08-322786 | 12/1996 |
| JP | 09-028662 | 2/1997 |
| JP | 10337274 | 12/1998 |
| JP | 11042258 | 2/1999 |
| JP | 2001-046318 | 2/2001 |
| SU | 871786 | 10/1981 |
| SU | 1256955 | 9/1986 |
| SU | 1301701 | 4/1987 |
| WO | WO 93/17751 A1 | 9/1993 |
| WO | WO 94/19051 A1 | 9/1994 |
| WO | WO 95/04556 A2 | 2/1995 |
| WO | WO 95/09562 A1 | 4/1995 |
| WO | WO 96/05768 A1 | 2/1996 |
| WO | WO 97/10746 A1 | 3/1997 |
| WO | WO 97/25101 A2 | 7/1997 |
| WO | WO 97/29701 A1 | 8/1997 |
| WO | WO 97/29710 A1 | 8/1997 |
| WO | WO 98/24017 A2 | 6/1998 |
| WO | WO 98/49938 A1 | 11/1998 |
| WO | WO 99/16359 A1 | 4/1999 |
| WO | WO 99/33392 A1 | 7/1999 |
| WO | WO 99/51283 A2 | 10/1999 |
| WO | WO 99/59664 A1 | 11/1999 |
| WO | WO 00/10456 A1 | 3/2000 |
| WO | WO 00/27462 A1 | 5/2000 |
| WO | WO 00/54653 A1 | 9/2000 |
| WO | WO 00/74565 A1 | 12/2000 |
| WO | WO 01/49353 A2 | 7/2001 |
| WO | WO 01/67964 A2 | 9/2001 |
| WO | WO 01/70096 A1 | 9/2001 |
| WO | WO 01/70097 A1 | 9/2001 |
| WO | WO 01/74235 A1 | 10/2001 |
| WO | WO 01/80935 A1 | 11/2001 |
| WO | WO 02/24058 A2 | 3/2002 |
| WO | WO 02/39909 A1 | 5/2002 |
| WO | WO 02/47549 A1 | 6/2002 |
| WO | WO 02/064028 A1 | 8/2002 |
| WO | WO 02/068988 A1 | 9/2002 |
| WO | WO 02/069841 A2 | 9/2002 |
| WO | WO 02/089692 A1 | 11/2002 |
| WO | WO 02/096276 A1 | 12/2002 |
| WO | WO 03/028547 A2 | 4/2003 |
| WO | WO 03/073920 A2 | 9/2003 |
| WO | WO 03/073921 A1 | 9/2003 |
| WO | WO 03/092476 A2 | 11/2003 |
| WO | WO 2004/006980 A2 | 1/2004 |
| WO | WO 2004/019769 A1 | 3/2004 |
| WO | WO 2004/049905 A2 | 6/2004 |
| WO | WO 2004/071284 A1 | 8/2004 |
| WO | WO 2004/080313 A1 | 9/2004 |
| WO | WO 2004/084702 A1 | 10/2004 |
| WO | WO 2005/084542 A1 | 9/2005 |
| WO | WO 2006/134881 | 12/2006 |

OTHER PUBLICATIONS

Belson et al; U.S. Appl. No. 11/796,220 entitled "Steerable segmented endoscope and method of insertion," filed Apr. 27, 2007.

Woodley et al; U.S. Appl. No. 11/871,104 entitled "System for managing bowden cables in articulating instruments," filed Oct. 11, 2007.

Berger, W. L. et al. Sigmoid Stiffener for Decompression Tube Placement in Colonic Pseudo-Obstruction. Endoscopy. 2000; 32 (1): 54-57.

Hasson, H.M. Technique of open laralscopy:equipment and technique. (from step 1 to step 9). May 1979, 2424 North Clark Street, Chicago, IL 60614. 3 pages.

Lee, et al. A highly redundant robot system for inspection. Proceedings of Conference on Intelligent Robotics in Field, Factory, Service, and Space (CIRFFSS "94). Mar. 21-24, 1994. 1:142-148. Houston, Texas.

McKernan, et al. Laparoscopic general surgery. Journal of the Medical Association of Georgia. 1990; 79 (3):157-159.

Science & Technology, Laptop Magazine. Oct. 2002. p. 98.

Slatkin, et al. The development of a robotic endoscope. Proceedings 1995 IEEE/RSJ International Conference on Intelligent Robots and Systems. Aug. 5-9, 1995. 2:162-171. Pittsburgh, Pennsylvania.

Supplementary European Search Report and Written Opinion for European Patent Application No. 06838212.6, mailed Aug. 22, 2011, 10 pages.

* cited by examiner

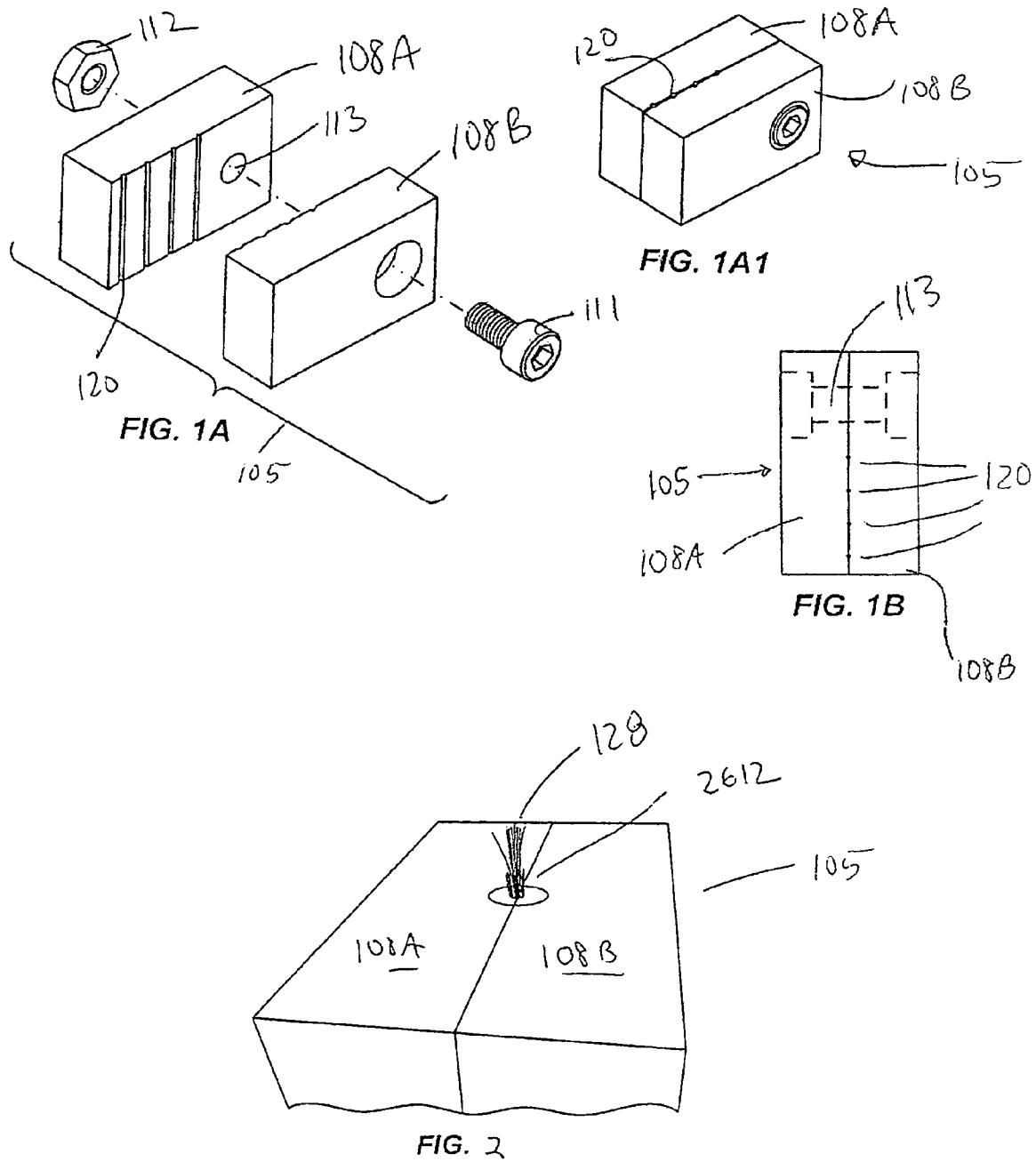

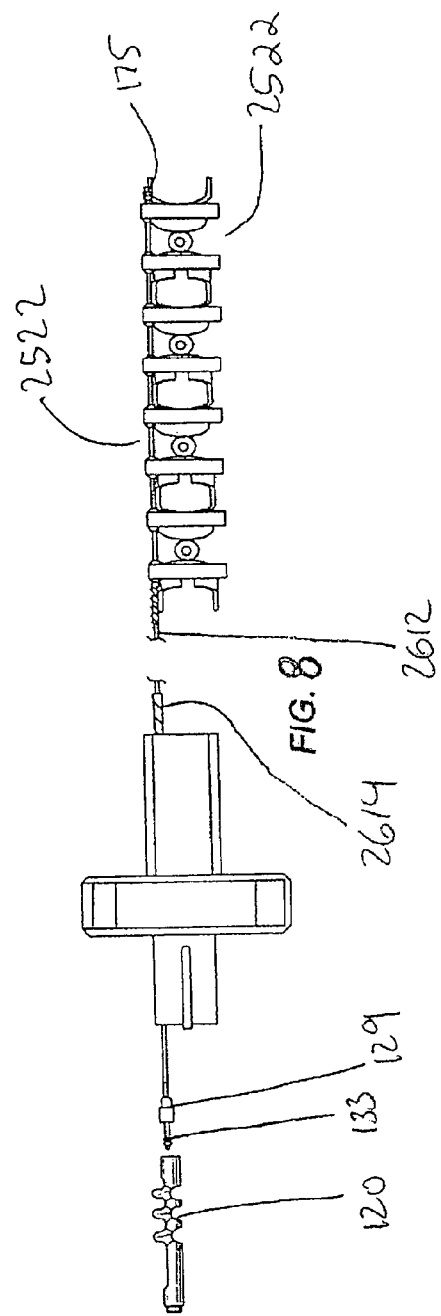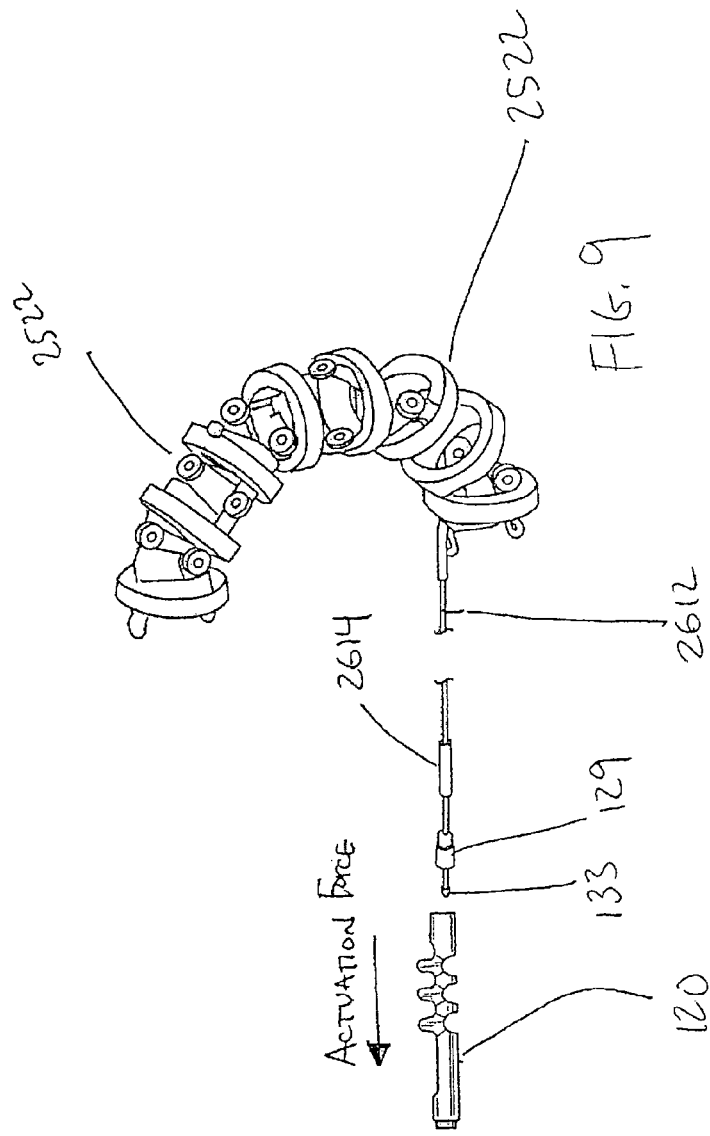

NON-METALLIC, MULTI-STRAND CONTROL CABLE FOR STEERABLE INSTRUMENTS

CROSS-REFERENCE TO RELATED APPLICATIONS

This application claims the benefit of U.S. Provisional Application No. 60/739,250 filed Nov. 23, 2005, titled, "Improved Tendon For Steerable Instruments" which is incorporated herein by reference in its entirety.

BACKGROUND OF THE INVENTION

One technique for transmitting actuation forces to the moveable segments of articulating instruments involves the use of a cable within a housing or a coil tube. This arrangement is commonly referred to as a Bowden cable and is similar in operation to a brake system on bicycle. This cable is used to transmit an actuation force from a control handle out to a steerable active segment. In some cases the forces needed to maneuver a steerable instrument can be large. In some cases, the large actuation force results from friction between the steel cable and the coil tube. It is desirable to reduce the amount of force the frictional forces in the cable/tube arrangement including the use of lubricants such as, for example, molybdenum disulfide.

However useful the lubricants may be, a number of practical challenges remain, such as, for example: (1) the molybdenum disulfide lubricant in powder form will eventually wear out with use of the scope causing degradation of scope performance; (2) the molybdenum disulfide lubricant is difficult to apply inside the coil and is messy during application; (3) the addition of any lubricant between cable and coil tube also causes lubrication issues between each of the coils of the coil tube allowing them to slip over each other under compressive loads. Coil tube buckling rapidly degrades endoscope performance and require expensive rebuilt of the scope coils.

What is needed is an improved way of overcoming the friction forces associated with transmitting actuation forces to the moveable segments of an articulating instrument. strand non-metallic braid while maintaining the diameter of the bonded area the same as or less than the diameter of either the non-metallic multi-strand braid or the lead line. Next, advance the multi-strand non-metallic braid through a coil tube using the lead line. In one alternative, the lead line is altered before the bonding step to improve adhesion to the non-metallic multi-strand braid. In another alternative, the bonding step includes gluing one end of the lead line to one end of a multi-strand non-metallic braid. In another alternative, the bonding step includes thermally bonding one end of the lead line to one end of a multi-strand non-metallic braid. In one aspect, a strand of the multi-strand braid is cut before the bonding step. In another embodiment, before the bonding step, placing one end of the lead line and one end of the non-metallic multi-strand braid into a fixture. In one aspect, the diameter of one end of the lead line or one end of the non-metallic multi-strand braid is reduced before bonding the lead line and the non-metallic multi-strand braid. In one aspect, the lead line is formed from the same material as the non-metallic multi-stranded braid.

In another aspect, the end of the multi-strand non-metallic braid is terminated. In one aspect, terminating includes forming a knot in the multi-strand non-metallic braid. In another aspect, the multi-strand non-metallic braid is passed through a threaded element before the terminating step. Termination may be accomplished by applying an adhesive to the knot formed in the multi-strand non-metallic braid, gluing a ball within the multi-strand non-metallic braid, securing a crimp to the multi-strand non-metallic braid or forming a loop in one end of the multi-strand non-metallic braid.

In another embodiment, there is provided a steerable instrument having a plurality of hinged segments; a multi-strand non-metallic braid connected distally to one segment of the plurality of segments and proximally to an actuator; and a steering controller adapted to control the actuator to move the hinged segment using the multi-strand non-metallic braid. In one aspect, a connector assembly couples the multi-strand non-metallic braid to the actuator. In another aspect, there is a carriage assembly in the connector and attached to one end of the multi-strand non-metallic braid. In another aspect, the multi-strand non-metallic braid passes through a coil tube extending between the connector assembly and the segment. In one alternative, the ratio of the clearance between the multi-strand non-metallic braid and the interior surface of the coil tube to the inner diameter of the coil tube is less than or equal to 15%. In one embodiment, the multi-strand non-metallic braid comprises ultra high molecular weight polyethylene (UHMWPE). In one aspect, the multi-strand non-metallic braid is connected distally to one segment of the plurality of segments by terminating the multi-strand non-metallic braid at the desired segment. In another aspect, there is a threaded element on the one end of the multi-strand non-metallic braid to attach the one end of the multi-strand non-metallic braid to the carriage assembly. In another aspect, there is a knot formed in the multi-strand non-metallic braid positioned between the threaded element on the one end of the multi-strand non-metallic braid and the carriage assembly. In one embodiment, there is a knot formed in the multi-strand non-metallic braid. In one aspect, there is an adhesive applied to the knot. In another aspect, the adhesive contains a pigment that provides a visual indication that the adhesive is present.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 1A, 1A1 and 1B illustrate various views of a fixture used to bond a leader to an braid structure.

FIG. 2 illustrates altering the end of a braid prior to bonding.

FIG. 8 illustrates a braid connected to a segmented, hinged instrument.

FIG. 9 illustrates using the braid to articulate the instrument in FIG. 8.

DETAILED DESCRIPTION OF THE INVENTION

The use of braided Ultra-High Molecular Weight Polyethylene (UHMWPE) is proposed as replacement for conventional stainless steel control cables. UHMWPE force transmissions cables may be used without additional lubrication. Our testing has demonstrated that the use of UHMWPE without additional lubrication reduces frictional forces as compared to the use of other cable material types such as steel. As a result, the reduced frictional load on the UHMWPE/coil tube configuration translates into a substantial reduction of the actuation forces required to steer the endoscope. In addition, the interior of the cable housing or coil tube may also be made of or have a coating of material to further reduce the friction between the UHMWPE cable and the housing.

Replacement of Steel Cables with Braided UHMWPE

Through extensive testing of various materials, it was found that braided UHMWPE purchased under the trade name of either Spectra® made by Honeywell in the United States or Dyneema® made by DSM in the Netherlands could substantially reduce the forces required to actuate the steerable segments of an endoscope. Additional details of the physical properties of UHMWPE are available in commercial references. Additional details are available via the Honeywell and DSM websites. The lubricity of the material allows it to be used without the need for lubrication in the coil tube resulting in more reliable force transmission elements with longer intervals between required servicing as compared to conventional steel cables. The resulting lower force also solves the problem of buckling the coil tubes. The construction of the pre-stretched, high denier braid of UHMWPE contributes to minimizing the lost motion in the system.

Method of Threading Braided UHMWPE Through Coil Tubes

One challenge to overcome when attempting to use a braided material to replace the conventional steel cable is the means of threading the limp braid through a coil tube. In some cases the coil tube may be as long as 110 inches and have an inside diameter of 0.025 inch.

This problem was solved in a novel way by first joining a lead line onto the braid. The addition of the lead line allowed the braid to be maneuvered through the coil tube. The method included bonding one end of a lead line to one end of a multi-strand non-metallic braid while maintaining the diameter of the bonded area the same as or less than the diameter of either the non-metallic multi-strand braid or the lead line. Once bonded with a diameter small enough to traverse the coil tube without undue friction, the lead line was used to advance the multi-strand non-metallic braid through the coil tube.

The lead line could be anything joined to the braid to assist in threading the braid structure into the tube. In one case, the lead line to assist in braiding was a monofilament line joined to the end of the UHMWPE braid. In one embodiment, the lead line is formed from the same material as the non-metallic multi-stranded braid.

Figure 6:
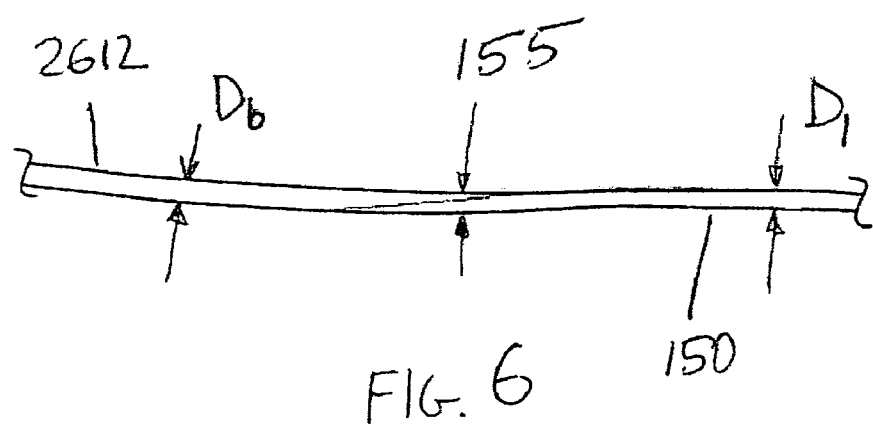
FIG. 6 illustrates the diameters of the leader, the braid and a bonded area.

This monofilament line could then be threaded through the coil tube and used to pull the UHMWPE braid through as well. This method required bonding the monofilament line to the braid without allowing the diameter of the bond to be larger than the inner dimension of the coil tube being used. Maintaining the size of the diameter of the bonding area may be accomplished by reducing the diameter of one end of the lead line, reducing the diameter of the non-metallic multi-strand braid or both before bonding the lead line and the non-metallic multi-strand braid. FIG. 6 illustrates how the diameter of the braid ($D_b$) and the diameter of the leader ($D_1$) are the same as the diameter of the bonding area 155. Additionally, bonding channels 120 may also be sized and dimensioned to maintain the diameter of each of these parts of the bonded structure so that will pass through a coil tube 2614. In one specific embodiment where the coil tube had an inner diameter of 0.025 inch and the diameter of the bonding area 155 was maintained at a diameter less than approximately 0.024 inch. Additional details of this challenge are detailed below with regard to FIGS. 7A and 7B.

Figure 3A:
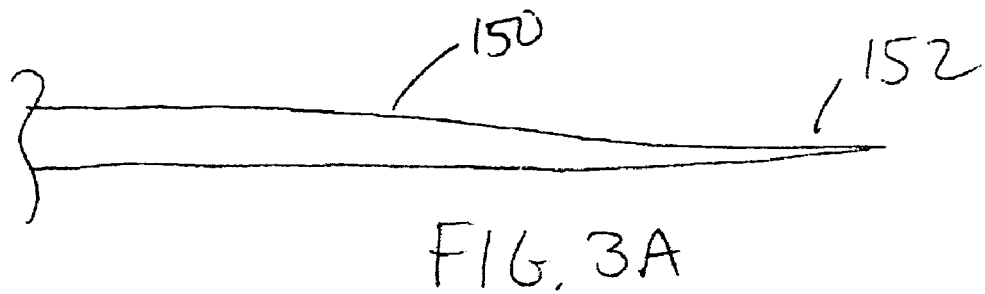
FIGS. 3A and 3B illustrate different altered leaders.
Figure 3B:
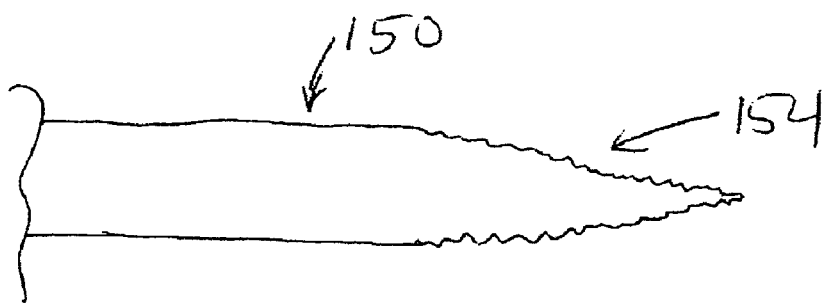
Figure 4:
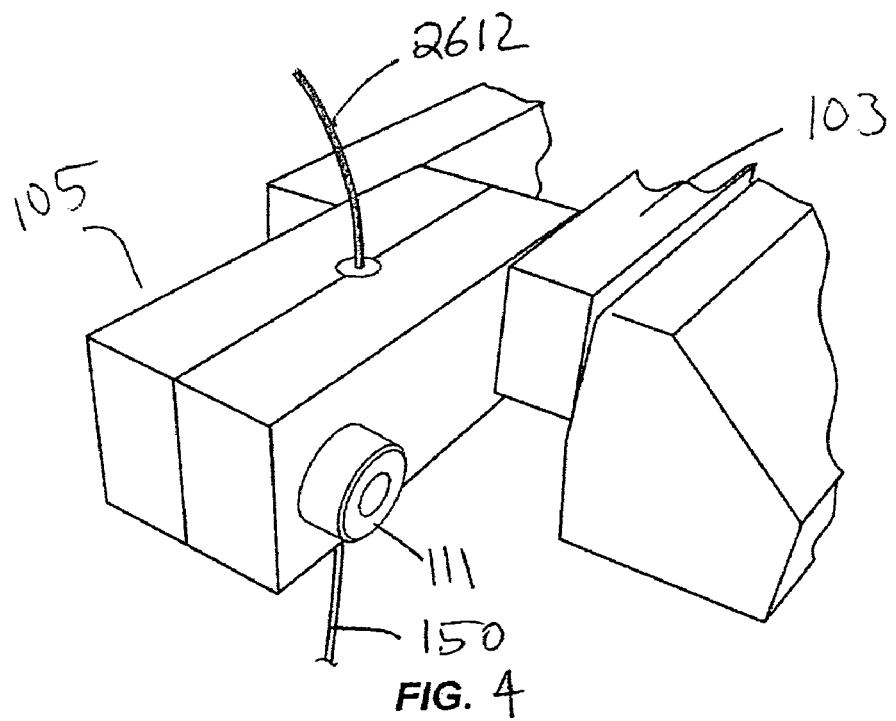
FIG. 4 illustrates the fixture of FIGS. 1A-1B in a vise during a bonding operation.

FIGS. 1-5 will now be used to illustrate one proposed bonding solution involving a bonding fixture was designed out of blocks of PTFE (i.e., Teflon®). Fabricating the fixture out of PTFE or other material that will not bond to the leader or the braid allows the bonding of the leader to the braid while being able to control the diameter of the bonding area. FIGS. 1A, 1A1 and 1B illustrate various views of the bonding fixture 105 made from complementary blocks 108A and 108B having a plurality of bonding channels 120. FIG. 1A is an exploded view of the components. FIG. 1A1 illustrated the assembled fixture 105. FIG. 1B illustrates the assembled fixture with a view of the opening 113. The blocks are secured together using conventional means such as a bolt 110 passed through opening 113 and secured by nut 112. The blocks may also or alternatively be secured using a vise 103 as shown in FIG. 4.

As shown in FIG. 2, a multi-strand non-metallic braid 2612 is shown inserted into an assembled fixture 105. This is the first step in the placing one end of the lead line and one end of the non-metallic multi-strand braid into a fixture before bonding the leader to the braid.

Next, the end of the braid may be cut to help bond to the leader and also aid in keeping the size of the bonded area small. In one embodiment, there is a step of cutting a strand of the multi-strand braid before the bonding step. Alternatively, all but one strand of the braid was trimmed approximately ¼ inch from the end using a razor blade prior to assembling the braid in the fixture. The remaining strand is used to bond to the leader. This cut end 128 is shown sticking up from the fixture 105 in FIG. 2. The next step is gluing one end of the lead line to one end of a multi-strand non-metallic braid. This may be accomplished with a drop of cyanoacrylate glue (such as commercially available Loctite 420) placed on the end of the braid 128.

Thereafter, the braid 2612 is pulled down into the fixture 105. The leader line 150 is then placed into the same bonding channel 120 as the braid 2612 as shown in FIG. 4. The leader 150 is advanced to meet the braid 2612 and any excess glue is wicked away. As shown in FIG. 3A, the leader 150 may have a reduced or shaped end 152 to aid in bonding to the braid while also keeping the bonded area diameter appropriately sized. Alternatively, as best seen in FIG. 3B, the leader 150 may have a reduced shape and a textured surface 154 to aid in bonding to the braid. As can been seen, the method includes altering one end of the lead line before the bonding step to improve adhesion to the non-metallic multi-strand braid.

Figure 5:
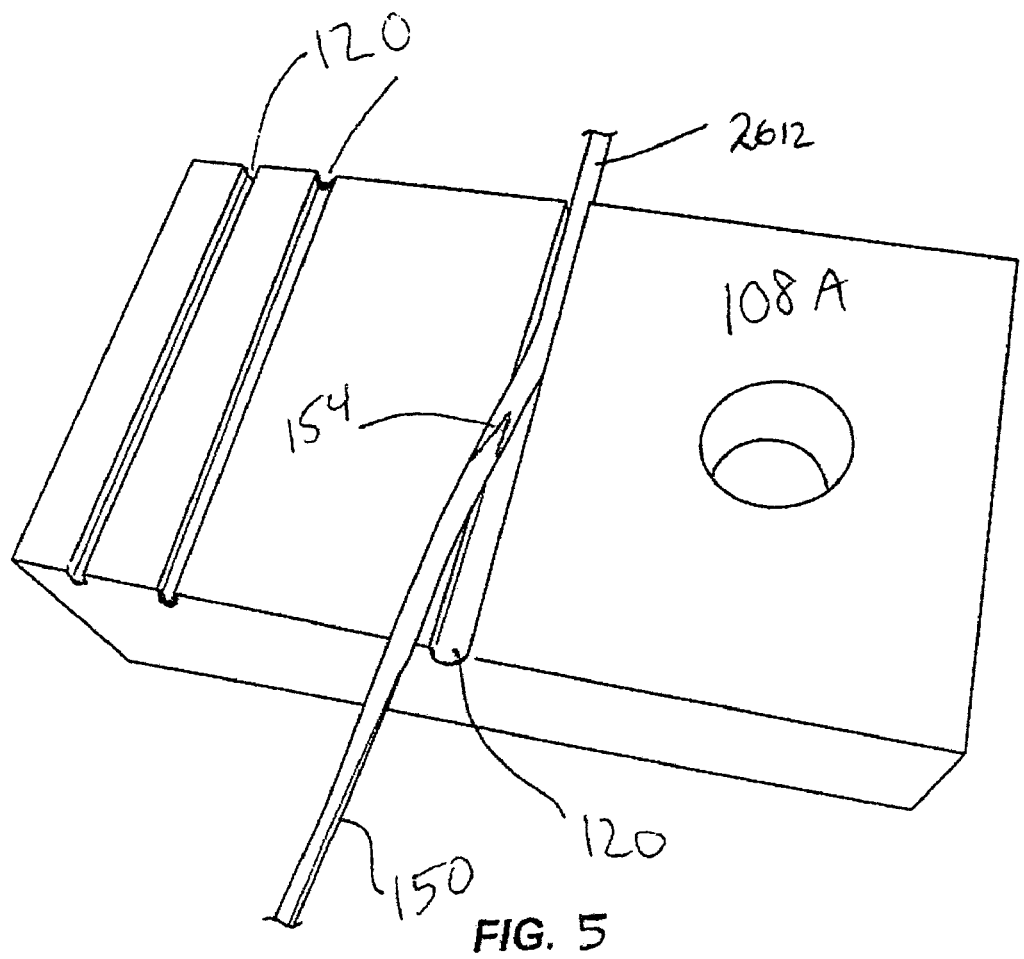
FIG. 5 illustrates a strand bonded to a leader being removed from a fixture.

After the glue dries, the braid 2612 with the attached leader 150 (i.e., the monofilament line in this example) is removed from the 2-piece fixture as shown in FIG. 5.

Once the monofilament leader is fixed to the end of the braid as best seen in FIG. 5, it can then be readily threaded through multiple lengths of coil tube 2614. Each time, the end of the braid 2612 can be cut to length and the assembly (i.e., the leader bonded to the braided structure) used to thread additional coils 2614. For example, the monofilament line 150 can be bonded to a 55 foot spool of braided UHMWPE that can be used to thread more than 50 feet of coil tubes 2614. The ability to make large lengths of the braided/tube assembly will greatly simplify the fabrication process used to make steerable instruments articulated using the non-metallic braid structure.

Alternatively, bonding the leader to the braid may be accomplished using other known bonding techniques such as thermal bonding or other techniques known to those of ordinary skill in the art to join the material type of the leader onto the UHMWPE braid. One of ordinary skill will appreciate that the bonding technique will depend on the types of material to be joined. The Beahm Split Die Thermal Bonder 220-B is a commercially available unit that may be well suited to a thermal bonding technique. As such, the bonding step may also include thermally bonding one end of the lead line to one end of a multi-strand non-metallic braid.

Method of Terminating the Braided UHMWPE

While useful in reducing friction in articulation forces, the lubricity of the UHMWPE braid makes it difficult to terminate the ends of the braid in a precise location.

One solution to the termination challenge was the realization that the braided UHMWPE can be terminated by simply knotting it off, or using other techniques known for securing braids of this type. As such, terminating an end of the multi-strand non-metallic braid may include forming a knot in the multi-strand non-metallic braid.

Alternatively, the knotted end could be further secured by gluing the braid together or other techniques to terminate the end of the line. As such, terminating the braid may include applying an adhesive to the knot formed in the multi-strand non-metallic braid. One cyanoacrylate used was Loctite® brand 420 series adhesive. Alternatively, for ease of manufacturing, a pigment may be added to the adhesive to provide a visual sign whether glue was applied to each knot 133. This is an improvement over clear glue that is difficult to tell if it has been applied to each knot. In an alternative embodiment, the adhesive applied to the terminated end is an ultraviolet cured adhesive such as an epoxy.

One exemplary technique is the use of a stopper knot soaked in a low viscosity, high wicking cyanoacrylate glue. The stopper knot, also known as a double overhand knot, as well as other suitable knots are described in a number of references.

Figure 7A:
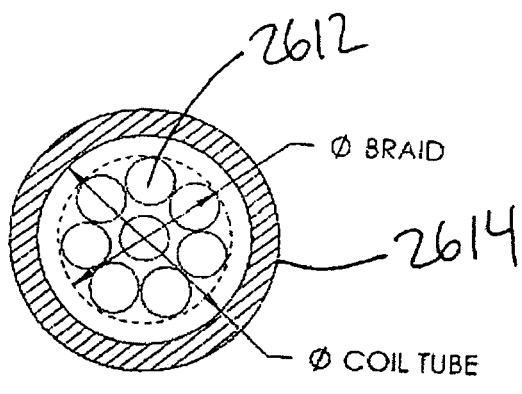
FIGS. 7A and 7B illustrate a cross section view of a braid in a coil tube.
Figure 7B:
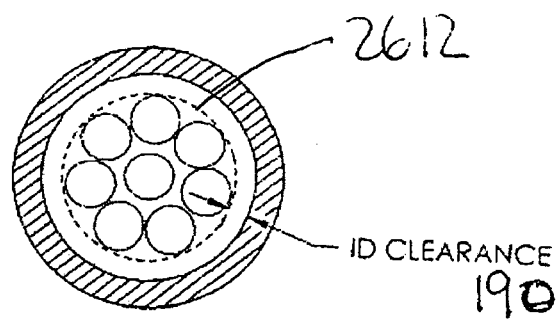

FIGS. 7A and 7B illustrate a braid 2612 within a coil tube 2614 having a clearance 190 between the braid and the interior surface of the coil tube. The inner diameter of the coil tube and the diameter of the coil tube are also indicated. Maintaining the appropriate inner diameter clearance 190 was another challenge solved using the methods of the invention. If the clearance 190 is too small, then the friction forces on the braid are high leading to the need for increased actuation forces. If the clearance is too large, the pulling on the braid to actuate a segment may cause the coil tube to buckle. Maintaining the proper clearance 190 is important to ensuring acceptable force transmission function. Consider the following specific examples for coil tubes having an inner diameter of 0.040 inch. A clearance of 0.001 inch will result in too much friction. A clearance of more than 0.007 inch results in buckling and herniation. The acceptable range of force transmission is between greater than 0.001 inch and less than 0.007 inch. Coil tubes in the size range are typically needed given the number of control cables 2612 used in the controllable instruments described below (i.e., up to 64 control cables used to control a fully articulated instrument). Numerous manufacturing challenges related to maintaining a small bonding area while working with small diameter braids have been solved by the methods described herein. As such, we have found that the ratio of the clearance between the multi-strand non-metallic braid and the interior surface of the coil tube to the inner diameter of the coil tube is less than or equal to 15%.

An exemplary UHMWPE cable is shown with an articulating instrument in FIGS. 8-14. As best seen in FIG. 8, a standard 2-56 set screw 129 was drilled through allowing the braided UHMWPE 2612 to be passed through the screw 129 and terminated using the stopper knot 133. The screw 129 could then be inserted in the end of a threaded carriage assembly 120 that is part of a rack or connector (further described in U.S. Patent Application Publication US 2006/0052664). The UHMWPE cable 2612 is pulled with an actuation force to activate each segment individually as described below.

As detailed above, the multi-strand non-metallic braid is connected distally to one segment of the plurality of segments by terminating the multi-strand non-metallic braid at the desired segment. Alternate termination methods include:

1. Full strength loop manufactured in one end of the braided cable.
2. Steel crimp of adequate length, with "toothed" or rough interior capable of holding the UHMWPE securely in place. Alternatively, a brass crimp with a smooth interior may be used.
3. Metal ball placed inside the hollow braid, then glued in place to terminate.

Steerable Instruments and System Using UHMWPE

There are a number of steerable instruments available. Examples of steerable instruments, various control, and force transmission systems are described in, for example, U.S. Pat. Nos. 6,468,203; 6,858,005 and U.S. patent application Ser. No. 10/988,212 filed Nov. 12, 2004, now U.S. Patent Application Publication US 2006/0052664, titled "Articulatable Connector Device for Endoscopes" each of which is incorporated herein by reference in entirety. The application and patents listed above are commonly assigned with this application.

FIGS. 8 and 9 illustrate a plurality of hinged segments 2522 and a multi-strand non-metallic braid 2612 connected distally to one segment of the plurality of segments (i.e., via knot 175) and proximally to an actuator as described below. In this illustrative portion of the system, the braid 2612 is terminated proximally at knot 133. The screw 129 is threaded into the rack or connector 120 so that the knot is maintained between the threaded connector and the rack. Not shown in this figure but described below is a steering controller adapted to control the actuator to move the hinged segment 2522 using the multi-strand non-metallic braid 2612. Application of an actuation force (shown by arrow in FIG. 9) to the rack 120, pulls the braid 2612 to bend the segment 2522 as shown.

Additional details of the use of the non-metallic braided structures described herein will be appreciated through reference to FIGS. 10-14.

Figure 10:
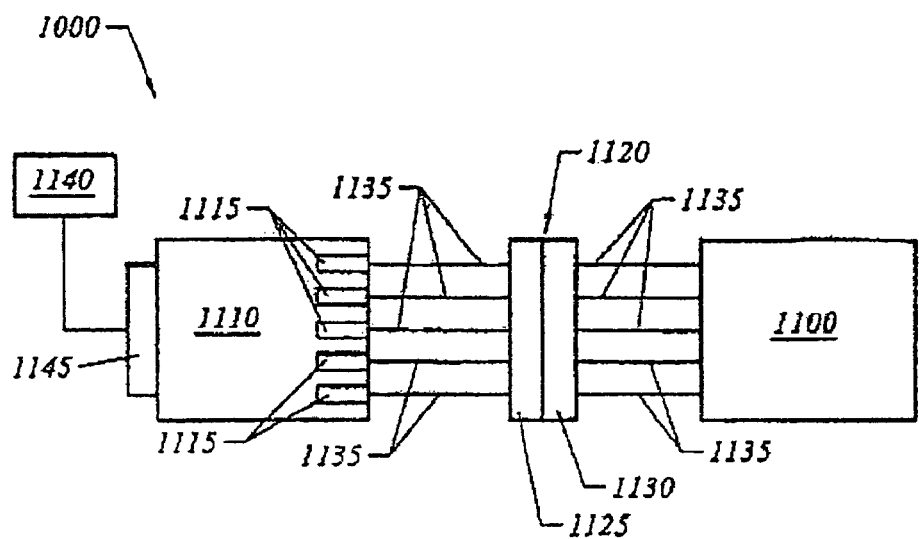
FIG. 10 shows a schematic view of a system for articulating a controllable article or bendable instrument.

FIG. 10 illustrates a schematic view of a system 1000 for moving a controllable article 1100. A force generator under control of one or both of a user input device 1140 and a system controller 1145 generates forces that are used to move the controllable article 1100. The forces generated by the force generator are transmitted to the controllable article using force connecting elements 1135 and a connector assembly 1120. The controllable article may also be an articulating instrument or a bendable instrument.

A connector assembly 1120 completes the transmission of power generated by the force generator 1110 and applied to the controllable article 1100. The two portions 1125, 1130 of the connector assembly 1120 are disengagably coupled. The connector portion 1125 is the first connector portion or the force generation side connector. The connector 1130 is the second connector portion or the controllable article side connector portion. When the connector portions 1125, 1130 are in a coupled condition, the force transmission elements 1135 are joined and force generated by the force generator 1110 is applied to the controllable article 1100. When the connector portions 1125, 1130 are not coupled, the connector portion 1130, force transmission elements. 1135 and the controllable article 1100 may be removed, in some embodiments as a single integrated unit, from the connector portion 1125, force transmission elements 1135 and the force generator 1110 or actuators 1115. The force transmission element 1135 may be a non-metallic braided cable such as the UHMWPE cable described herein.

The connector assembly 1120 provides the ability to quickly connect and disconnect the two portions 1125, 1130 allows a single force transmission portion to be used with multiple controllable articles. Currently, articulating instruments such as, for example, endoscopes typically have only 4 cables to provide limited control at the tip of the endoscope. Moreover, the connector provides compact organization and efficient coupling of numerous force transmission elements used by highly maneuverable controllable articles. The controllable articles described herein may use 16 or more UHMWPE control cables or 4 UHMWPE control cables per segment and 4 or more segments. In one embodiment, there are 32 UHMWPE cables used to control a fully segmented controllable instrument. In another embodiment, there are 64 UHMWPE cables used to control a fully segmented controllable instrument.

Figure 11:
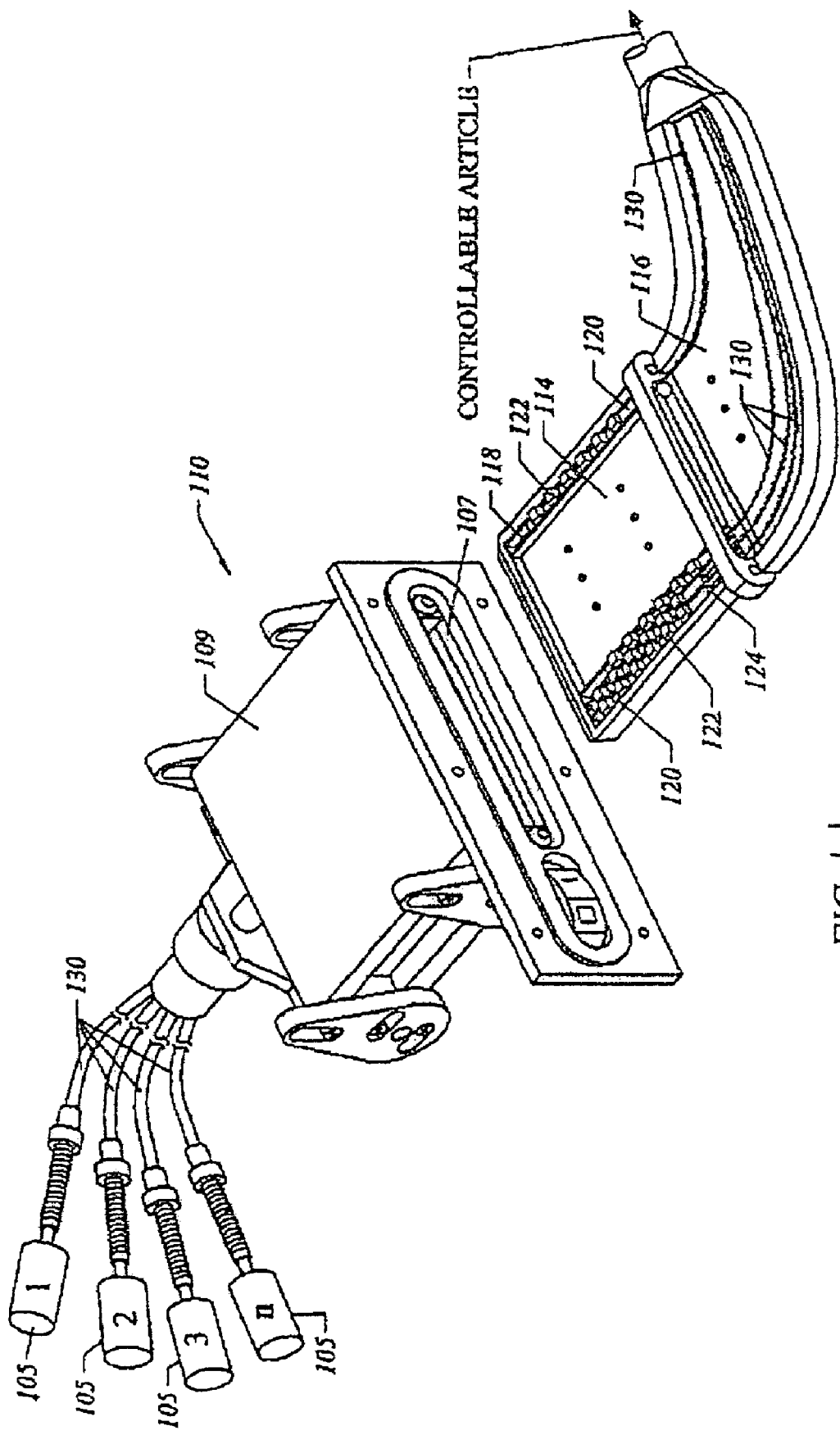
FIG. 11 is a perspective view of a connector assembly.

FIG. 11 illustrates a perspective view of a connector assembly 110 according to one embodiment of the present invention. The connector assembly 110 includes a first connector portion 112 (not shown but within housing 109) and a second connector portion 114. The first connector portion 112 is within the housing 109. The second connector assembly 114 includes a plurality of guide ways 118 each containing a carriage assembly 120. Each carriage assembly contains one or more than one engaging feature 122. Engaging features 122 on carriage assemblies 120, in the second connector portion 114 are adapted to engage with the engaging features 122 on carriage assemblies 120 of the first connector portion 112. One end of the carriage assemblies is connected to force transmission elements or UHMWPE cables 130. In the illustrated embodiment, the cables are Bowden cables. The cables run through a slack area 116. The slack area 116 allows added space for cable slack that may build up during controllable article movement. Thereafter, the UHMWPE cables are terminated and connected as desired to a specific segment of the controllable article.

The housing 109 provides a structural base for supporting the connector assembly 110. In this embodiment, the first connector portion 112 (not shown) is secured within the housing 109. The first connector portion and its carriage assemblies are connected via force transmission elements 130 to actuators 105. While four actuators 105 are illustrated, it is to be appreciated that more actuators may be used to drive a corresponding number of carriage assemblies. The housing 109 also provides a opening 107 configured to receive the second connector portion 114. Optionally, either one or both of the opening 107 or a portion of the second connector portion 114 may be keyed to ensure correct orientation prior to connection. When the second connector portion 114 is placed within the opening 107, the first and second connector portions 112, 114 are brought into engagement using an appropriate quick release mechanism, such as for example a cam actuated lever or other engagement device as known to those of ordinary skill in the art. When the first and second connector portion 112, 114 are engaged, forces generated by actuators 105 are transmitted to the controllable article.

Figure 12:
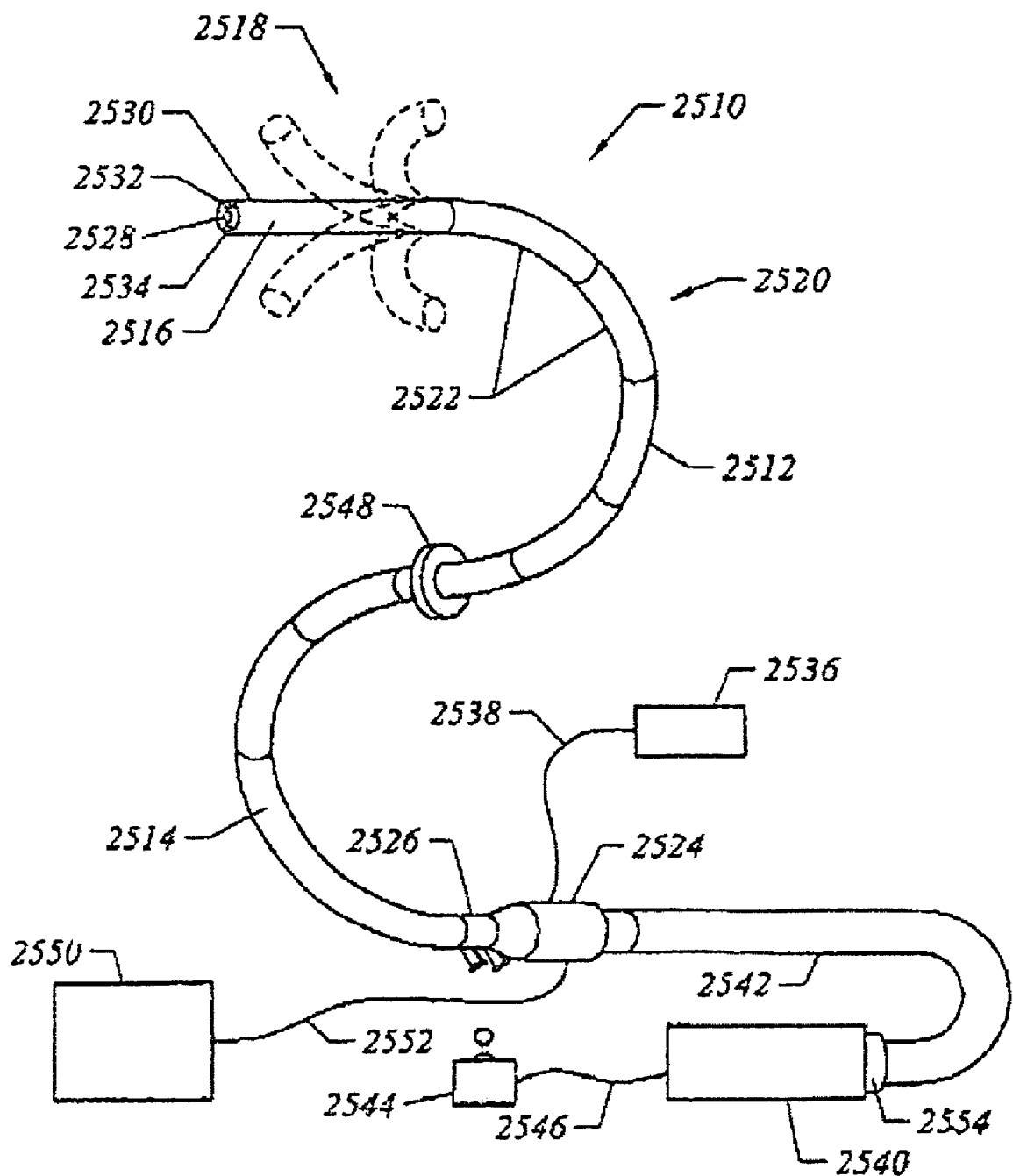
FIG. 12 illustrates an embodiment of a segmented endoscope.

FIG. 12 shows an embodiment where the controllable instrument is a tendon driven endoscope 2510. The endoscope 2510 has an elongate body 2512 with a manually or selectively steerable distal portion 2516, an automatically controlled portion 2520, and a flexible and passively manipulated proximal portion 2514, which may be optionally omitted from the device. The steerable distal portion 2516 can be articulated by hand (i.e., using mechanical force of a conventional endoscope manual controls adapted to articulate segments) or with mechanical assistance from actuators pulling on UHMWPE cables. In addition, some embodiments allow a user to input steering commands (i.e., via a joystick 2544 or other input device) into a controller that translates the steering commands into endoscope segment movement.

Figure 13:
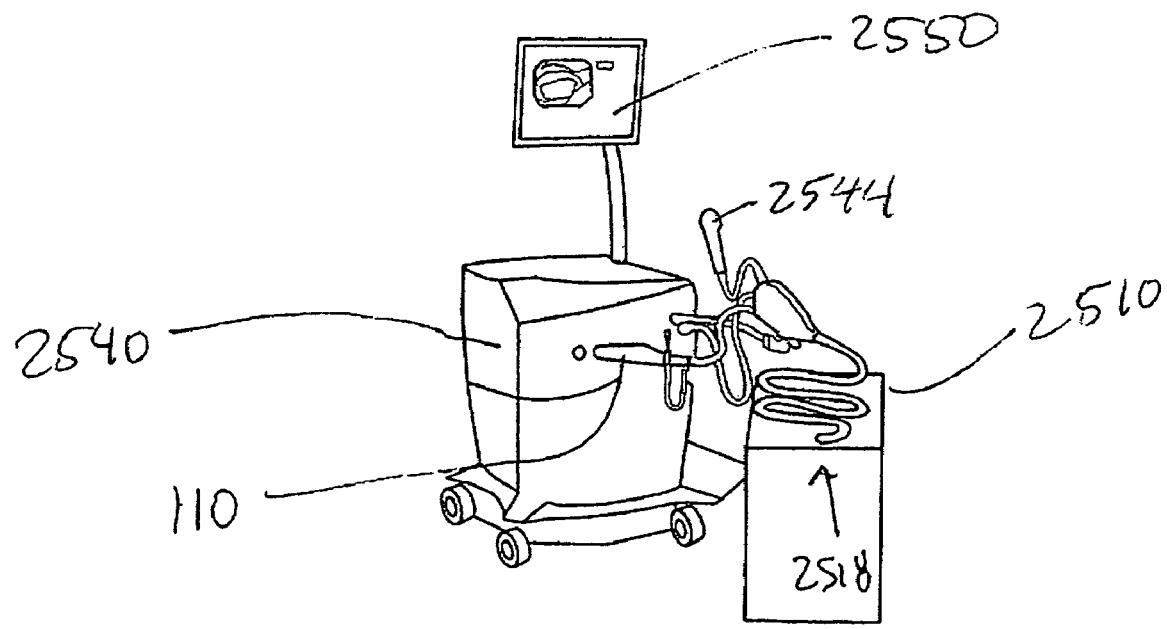
FIG. 13 illustrates an embodiment of a system used with an instrument of the invention.

The automatically controlled portion 2520 is segmented, and each segment is capable of bending through a fill range of steerable motion. The distal portion 2516 is also a controllable segment. A more detailed description on the construction and operation of the segmented endoscope may be found in U.S. patent application Ser. No. 10/229,577 filed Aug. 27, 2002, which is incorporated herein by reference in its entirety. Additional details of the arrangement of components are illustrated in FIG. 13 that illustrates an actual embodiment of a computer controlled endoscope and system described herein.

Returning now to FIG. 12, the selectively steerable distal portion 2516 can be selectively steered or bent up to, e.g., a full 180 degree bend in any direction 2518, as shown. A fiber optic imaging bundle 2534 and one or more illumination fibers 2532 may extend through the body 2512 from the proximal portion 2514 to the distal portion 2516. Alternatively, the endoscope 2510 may be configured as a video endoscope with a miniaturized video camera, such as a CCD or CMOS camera, positioned at the distal portion 2516 of the endoscope body 2512. The images from the video camera can be transmitted to a video monitor by a transmission cable or by wireless transmission where images may be viewed in real-time and/or recorded by a recording device onto analog recording medium, e.g., magnetic tape, or digital recording medium, e.g., compact disc, digital tape, etc. LEDs or other light sources could also be used for illumination at the distal tip of the endoscope.

The body 2512 of the endoscope 2510 may also include one or more access lumens 2528 that may optionally be used for illumination, fibers for providing a light source, insufflation or irrigation, air and water channels, and vacuum channels. Generally, the body 2512 of the endoscope 2510 is highly flexible so that it is able to bend around small diameter curves without buckling or kinking while maintaining the various channels intact. When configured for use as a colonoscope, the body 2512 of the endoscope 2510 may range typically from 135 to 185 cm in length and about 13-19 mm in diameter. The endoscope 2510 can be made in a variety of other sizes and configurations for other medical and industrial applications.

The controllable portion 2520 is composed of at least one segment 2522, and preferably several segments 2522, which are, controllable via a computer and/ore electronic controller 2540 located at a distance from the endoscope 2510. Each or at least a majority, of the segments 2522 may have UHMWPE force transmission elements or tendons mechanically connected to force generators or actuators to allow for the controlled motion of the segments 2522 in space. The actuators driving the UHMWPE tendons may include a variety of different types of mechanisms capable of applying a force to a tendon, e.g., electromechanical motors, pneumatic and hydraulic cylinders, pneumatic and hydraulic motors, solenoids, shape memory alloy wires, electronic rotary actuators or other devices or methods as known in the art. The linear translation of the actuators within the controller may be configured to move over a relatively short distance to accomplish effective articulation depending upon the desired degree of segment movement and articulation. The movement of the actuators may be measured using sensors to provide input to the control system.

Each segment 2522 preferably defines at least one lumen running throughout to provide an access channel through which wires, optical fibers, air and/or water channels, various endoscopic tools, or any variety of devices and wires may be routed. A polymeric covering, or sheath, 2530 may also extend over the body of the endoscope 2512 including the controllable portion 2520 and steerable distal portion 2516. This sheath 2530 can preferably provide a smooth transition between the controllable segments 2522, the steerable distal portion 2516, and the flexible tubing of proximal portion 2514.

A handle 2524 may be attached to the proximal end of the endoscope. The handle 2524 may include an ocular connected to the fiber optic imaging bundle 2534 for direct viewing. The handle 2524 may otherwise have a cable 2552 for connection to a video monitor, camera, e.g., a CCD or CMOS camera, or a recording device 2550. The handle 2524 may be connected to an illumination source 2536 by an illumination cable 2538 that is connected to or continuous with the illumination fibers 2534. Alternatively, some or all of these connections could be made at the controller 2540, luer lock fittings 2526 may be located on the handle 2524 and connected to the various instrument channels.

The handle 2524 may be connected to a motion controller 2540 by way of a controller cable 2542. A steering controller 2544 may be connected to the motion controller 2540 by way of a second cable 2546 or it may optionally be connected directly to the handle 2524. Alternatively, the handle may have the steering control mechanism integrated directly into the handle, e.g., in the form of a joystick, conventional disk controllers such as dials, pulleys or wheels, etc. The steering controller 2544 allows the user to selectively steer or bend the selectively steerable distal portion 2516 of the body 2512 in the desired direction 2518. The steering controller 2544 may be a joystick controller as shown, or other steering control mechanism, e.g., dual dials or rotary knobs as in conventional endoscopes, track balls, touch pads, mouse, or sensory gloves. The motion controller 2540 controls the movement of the segmented automatically controlled proximal portion 2520 of the body 2512. This controller 2540 may be implemented using a motion control program running on a microcomputer or using an application specific motion controller.

The actuators applying force to the tendons may be included in the motion controller unit 2540, as shown, or may be located separately and connected by a UHMWPE control cable. The UHMWPE tendons controlling the steerable distal portion 2516 and the controllable segments 2522 extend down the length of the endoscope body 2512 and connect to the actuators. FIG. 3 shows a variation in which the UHMWPE tendons may pass through the handle 2524 and connect directly to the motion controller 2540 via a quick-release connector 2554. In this embodiment, quick release connector 2254 could be any of the above described connector or engagement assemblies. In this variation, the UHMWPE tendons may be part of the control cable 2542, although they could independently connect to the actuators, so long as the actuators are in communication with the controller 2540.

An axial motion transducer (also called a depth referencing device or datum) 2548 may be provided for measuring the axial motion, i.e., the depth change, of the endoscope body 2512 as it is advanced and withdrawn. The depth referencing device 2548 can be made in many possible configurations. For example, the axial motion-transducer 2548 in FIG. 3 is configured as a ring 2548 that may surround the body 2512 of the endoscope 2510. The axial motion transducer 2548 is preferably attached to a fixed point of reference, such as the surgical table or the insertion point for the endoscope 2510 on the patient's body. Depth referencing device 2548, and different examples thereof; as well as segment articulation and cable operation are described in further detail in U.S. patent application Ser. No. 10/229,577 filed Aug. 27, 2002, which is incorporated herein by reference in its entirety.

Figure 14:
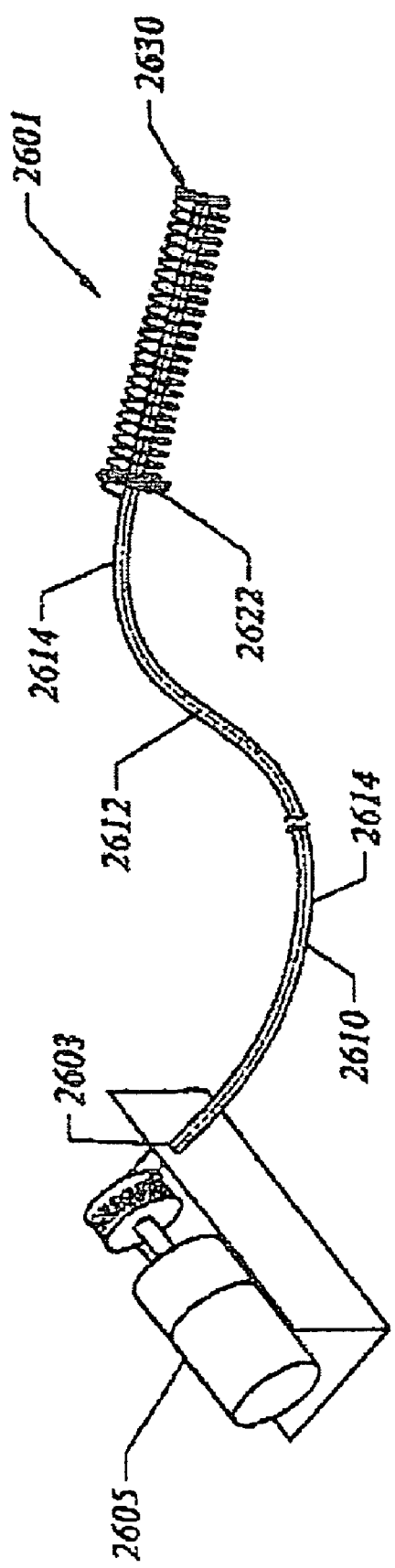
FIG. 14 shows a partial schematic representation of a single UHMWPE tendon connected to a segment and an actuator.

FIG. 14 shows a partial schematic representation of a single UHMWPE tendon coupled to a segment. For clarity, the other parts of a complete endoscope, including other tendons and segments, have been omitted from FIG. 4. Tension applied to a UHMWPE cable is transferred across the entire segment, resulting in bending. The Bowden cable 2610 has a coil tube 2614 attached to the base 2622 of the segment 2601 and also fixed at the proximal actuator end 2603. The UHMWPE cable 2612 is connected to the actuator 2605 and the distal segment end 2630. By applying tension to the UHMWPE cable 2612, only the intended segment 2601 is bent, and more proximal segments are unaffected. The UHMWPE cable 2612 is placed in tension by the actuator 2605, which is show in this variation, as a motor pulling on the UHMWPE cable 2612.

While numerous embodiments of the present invention have been shown and described herein, one of ordinary skill in the art will appreciate that such embodiments are provided by way of example only. Numerous variations, changes, and substitutions will now occur to those skilled in the art without departing from the invention. It should be understood that various alternatives to these embodiments of the invention described herein may be employed in practicing the invention. It is intended at the following claims defined the scope of the invention and it methods and structures within the scope of these claims and their equivalents be covered thereby.

What is claimed is:

1. A method for inserting a non-metallic multi-strand braid through a coil tube, the method comprising:
   bonding one end of a lead line to one end of a multi-strand non-metallic braid to create a bonded area, wherein the bonded area has a diameter that is the same as or less than the diameter of both the non-metallic multi-strand braid and the lead line; and advancing the multi-strand non-metallic braid through a coil tube using the lead line.

2. The method according to claim 1 further comprising: altering the one end of the lead line before the bonding step to improve adhesion to the non-metallic multi-strand braid.

3. The method according to claim 1 wherein the bonding step comprises gluing the one end of the lead line to the one end of a multi-strand non-metallic braid.

4. The method according to claim 1 wherein the bonding step comprises thermally bonding the one end of the lead line to the one end of a multi-strand non-metallic braid.

5. The method according to claim 1 further comprising: cutting a strand of the multi-strand braid before the bonding step.

6. The method according to claim 1 further comprising: placing the one end of the lead line and the one end of the non-metallic multi-strand braid into a fixture before the bonding step.

7. The method according to claim 1 further comprising: terminating an end of the multi-strand non-metallic braid.

8. The method according to claim 7 wherein terminating includes forming a knot in the multi-strand non-metallic braid.

9. The method according to claim 7 comprising: passing the multi-strand non-metallic braid through a threaded element before the terminating step.

10. The method of claim 8 further comprising applying an adhesive to the knot formed in the multi-strand non-metallic braid.

11. The method of claim 8 wherein terminating an end of the multi-strand braid comprises gluing a ball within the multi-strand non-metallic braid.

12. The method of claim 8 wherein terminating an end of the multi-strand non-metallic braid comprises securing a crimp to the multi-strand non-metallic braid.

13. The method of claim 8 wherein terminating an end of the multi-strand non-metallic braid comprises forming a loop in one end of the multi-strand non-metallic braid.

14. The method of claim 1 further comprising reducing the diameter of the one end of the lead line or the one end of the non-metallic multi-strand braid before bonding the lead line and the non-metallic multi-strand braid.

15. The method according to claim 1 wherein the lead line is formed from the same material as the non-metallic multi-stranded braid.

* * * * *